United States Patent
Groendahl

(10) Patent No.: US 6,297,243 B1
(45) Date of Patent: Oct. 2, 2001

(54) METHODS OF TREATING HOT FLASHES, ESTROGEN DEFICIENCIES AND DEFERRING MENOPAUSE BY THE ADMINISTRATION OF A LUTEINIZING HORMONE ANTAGONIST

(75) Inventor: Christian Groendahl, Vaerloese (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 09/182,766

(22) Filed: Oct. 29, 1998

Related U.S. Application Data

(63) Continuation of application No. PCT/DK97/00454, filed on Oct. 20, 1998
(60) Provisional application No. 60/063,433, filed on Oct. 29, 1997.

(30) Foreign Application Priority Data

Oct. 20, 1997 (DK) .................................................. 1197/97

(51) Int. Cl.⁷ ........................ A61K 31/50; A61K 31/495; A61K 31/505; A61K 31/44
(52) U.S. Cl. ......................... 514/247; 514/252; 514/254; 514/267; 514/299; 514/334; 514/874
(58) Field of Search ................................... 514/247, 252, 514/254, 267, 299, 334, 874

(56) References Cited

U.S. PATENT DOCUMENTS

| | | | |
|---|---|---|---|
| 4,363,809 | * 12/1982 | Marko et al. | 424/260 |
| 4,406,904 | 9/1983 | Welle et al. | 424/260 |

FOREIGN PATENT DOCUMENTS

WO 98/10765   3/1998   (WO).

OTHER PUBLICATIONS

Conn's Current Therapy, W.B. Sanders Co., Philadelphia, pp. 1017–1020, 1992.*

* cited by examiner

Primary Examiner—Kimberly Jordan
(74) Attorney, Agent, or Firm—Steve T. Zelson; Carol E. Rozek

(57) ABSTRACT

A pharmaceutical composition comprising a LH antagonist or a pharmaceutically acceptable salt thereof, and a pharmaceutically acceptable carrier is useful for deferring the onset of menopause.

10 Claims, No Drawings

METHODS OF TREATING HOT FLASHES, ESTROGEN DEFICIENCIES AND DEFERRING MENOPAUSE BY THE ADMINISTRATION OF A LUTEINIZING HORMONE ANTAGONIST

CROSS-REFERENCE TO RELATED APPLICATIONS

This application is a continuation of application no. PCT/DK97/00454 filed on Oct. 20, 1998 and claims priority under 35 U.S.C. 119 of U.S. provisional application Ser. No. 60/063,433 filed Oct. 29, 1997 and Danish application no. 1197/97 filed Oct. 20, 1997, the contents of which are fully incorporated herein by reference.

FIELD OF INVENTION

The present invention relates to a pharmaceutical composition, to use of luteinizing hormone (LH) antagonists for preparing a medicament for treatment of hot flushes or hot flashes (i.e., menopausal vaso-motor symptoms), to use of LH antagonists for preparing a medicament for treatment of estrogen deficiencies, to use of LH antagonists for preparing a medicament for decreasing the loss of follicles during the pre- and per-menopausal period, thereby deferring the onset of menopause and consequently the symptoms related to lack of estrogen. Furthermore the invention relates to use of LH antagonists for preparing a contraceptive.

BACKGROUND OF THE INVENTION

The mammalian female is born with a fixed and subsequently decreasing number of meiotically arrested oocytes in the ovaries. Oocytes encompassed by a single layer of flattened epithelial cells form primordial follicles and constitute the fixed resting pool of oocytes in the ovaries from which oocytes are recruited throughout the reproductive life. An unknown signal triggers a cohort of the primordial follicles to develop into primary, secondary and ultimately Graafian follicles.

Approximately one million primordial follicles is present in a human ovary in a newborn. The functional activity of the human ovary depends on the size of the follicle store. It has been speculated that a threshold exist of approximately 1000–2000 oocytes that mediates the onset of menopause or cessation of cyclic activity in the ovary (Gosden, 1996, Serono Symposium, Leeds).

The primordial follicles do not posses receptors for follicle stimulating hormone (FSH) or luteinizing hormone (LH); however, once the growing follicles have reached a certain size, gonadotropins are the major players that controls growth and ovulation. Early in reproductive life the primordial follicles are lost from the ovary at a relative constant rate. Around 35–40 years of age the rate of disappearance apparently accelerates. The reason for this dramatic loss is unknown.

The osteopenia that accompanies the menopause continues to represent a major public health problem. Left unchecked, the cumulative loss of bone can potentially compromise the skeleton's structural integrity, resulting in painful and debilitating fractures of the wrist, spine and femur. Efforts to reduce the risk and incidence of fractures have focused on the development of therapies that conserve skeletal mass by inhibiting bone resorption. Among various treatment modalities, estrogen remains the preferred means to prevent the development of post menopausal osteoporosis (Lindsey R, Hart D M, MacClean A 1978, "The role of estrogen/progestogen in the management of the menopause", Cooke I D, ed, Proceedings of University of Sheffield symposium on the role of estrogen and progestogen in the management of the menopause, Lancaster, UK: MTP Press Ltd. pp. 9–25; Marshall D H, Horsmann A, Nordin BEC1977, "The prevention and management of post-menopausal osteoporosis.", Acta Obstet Gynecol Scand (Suppl) 65:49–56; Recker R R, Saville P D, Heaney R P 1977, "Effect of estrogen and calcium carbonate on bone loss in post-menopausal women", Ann Intern Med. 87:649–655; Nachtigall L E, Nachtigall R H, Nachtigall R D, Beckman E M 1979, "Estrogen replacement therapy", Obstet Gynecol. 53:277–281) and it is now accepted that estrogens significantly decrease fracture incidence and risk (Krieger N, Kelsey J L, Holford T R, O'Connor T 1982, "An epidemiological study of hip fracture in postmenopausal women", Am J Epidemiol. 116:141–148; Hutchinson T A, Polansky S M, Feinstein A R 1979, "Post-menopausal estrogens protect against fractures of hip and distal radius: A case-control study", Lancet 2:705–709; Paginini-Hill A, Ross R K, Gerkins V R, Henderson B E, Arthur M, Mack T M 1981, "Menopausal oestrogen therapy and hip fractures", Ann Intern Med. 95:28–31; Weiss N S, Ure C L, Ballard J H, Williams A R, Daling J R 1980, "Decreased risk of fractures on the hip and lower forearm with post-menopausal use of estrogen", N Eng J Med. 303:1195–1198).

While the beneficial actions of estrogen on the skeleton are clearly significant, there is also considerable evidence for a positive effect of estrogen on the cardiovascular system. Previous studies have attributed these actions to estrogen's effects on serum lipids, but recent data has now shown that in addition to the effects on the lipid profile, estrogen can also directly influence vessel wall compliance, reduce peripheral resistance and prevent atherosclerosis (Lobo R A 1990, "Cardiovascular implication of estrogen replacement therapy", Obstetrics and Gynaecology, 75:18S–24S; Mendelson M E, Karas R H 1994, "Estrogen and the blood vessel wall", Current Opinion in Cardiology, 1994(9):619–626). Based on available epidemiological data, the overall impact of these physiological and pharmacological actions of estrogen is an age independent reduction in cardiovascular mortality and morbidity in women (Kannel W H, Hjortland M, McNamara P M 1976 "Menopause and risk of cardiovascular disease: The Framingham Study", Ann Int Med, 85:447–552). Furthermore, a more recent analysis has concluded that post-menopausal estrogen treatment reduces the risk of cardiovascular disease by approximately 50 percent (Stampfer M J, Colditz G A 1991, "Estrogen replacement therapy and coronary heart disease: a quantitative assessment of the epidemiological evidence", Preventive Medicine, 20:47–63.).

In addition to the positive effects of estrogen on bone and cardiovascular system, there is now data which indicate that the central nervous system can benefit from estrogen. Short term studies in human subjects have shown that increased levels of estrogen are associated with higher memory scores in post menopausal women (Kampen D L, Sherwin B B 1994, "Estrogen use and verbal memory in healthy post-menopausal women", Obstetrics and Gynecology, 83(6): 979–983). Furthermore, the administration of exogenous estrogen to surgically post menopausal women specifically enhances short-term memory. Moreover, the effects of estrogen on cognition do not appear confined to short-term effects as epidemiological findings indicate that estrogen treatment significantly decreases the risk of senile dementia-Alzheimers type in women (Paganini-Hill A, Henderson V W, 1994, "Estrogen deficiency and risk of Alzheimer's disease in women", Am J Epidemiol, 140:256–261; Ohkura T, Isse K, Akazawa K, Hamamoto M, Yoshimasa Y, Hagino N, 1995, "Long-term estrogen replacement therapy in female patients with dementia of the Alzheimer Type: 7 case reports", Dementia, 6:99–107). While the mechanism whereby estrogens enhance cognitive function is unknown, it is possible to speculate that the direct effects of estrogen on cerebral blood flow (Goldman H, Skelley E b, Sandman C A, Kastin A J, Murphy S, 1976, "Hormones and regional brain blood flow", Pharmacol Biochem Rev. 5(suppl 1):165–169; Ohkura T, Teshima Y, Isse K, Matsuda H, Inoue T, Sakai Y, Iwasaki N, Yaoi Y, 1995, "Estrogen increases cerebral and cerebellar blood flows in postmenopausal women", Menopause: J North Am Menopause Soc. 2(1) 13–18) and neuronal cell activities (Singh M, Meyer E M, Simpkins J W, 1995, "The effect of ovariectomy and estradiol replacement on brain-derived neurotrophic factor messenger ribonucleic acid expression in cortical and hippocampal brain regions of female Sprague-Dawley rats", Endocrinology, 136:2320–2324; McMillan P J, Singer C A, Dorsa D M, 1996, "The effects of ovariectomy and estrogen replacement on trkA and choline acetyltransferase mRNA expression in the basal forebrain of the adult female Sprague-Dawley rat", J Neurosci., 16(5):1860–1865) are potential effectors for these beneficial actions.

The beneficial effect of a prolonged stage of naturally occurring estrogens as a consequence of deferring the menopause are not limited to the chronic conditions described above. Indeed, the more traditional applications of estrogen therapies would include the following: relief of menopausal symptoms (i.e. flushing and urogenital atrophy); oral contraception; prevention of threatened or habitual abortion, relief of dysmenorrhea; relief of dysfunctional uterine bleeding; an aid in ovarian development; treatment of acne; diminution of excessive growth of body hair in women (hirsutism); treatment of prostatic carcinoma: and suppression of post-partum lactation [Goodman and Gilman, The Pharmacological Basis of Therapeutics (Seventh Edition) Macmillan Publishing Company, 1985, pages 1421–1423]. A "hot flush" is a sudden transient sensation ranging from warmth to intense heat and typically accompanied by flushing and perspiration. It is the classic sign of the menopause and the predominant complaint of menopausal women. Epidemiological studies report that the majority of menopausal women experience hot flushes, although with large variation in frequency and intensity (Treatment of the Postmenopausal Woman, Basic and Clinical Aspects, Raven Press 1994, ed. R. A. Lobo).

Even though the beneficial effects of sustained endogenous estrogen secretion on a wide variety of organ systems and tissues appear indisputable, the level and duration of estrogen exposure is also associated with an increased risk of endometrial hyperplasia and carcinoma. The use of concomitant cyclic progestins does reduce the risk of endometrial pathology, but this is achieved at the expense of the return or maintenance of regular menstruation, a result that is objectionable to many patients. In addition to estrogen's stimulatory effect on the endometrium, there remains considerable controversy regarding reports of an association between long-term estrogen exposure and an increased risk of breast cancer (Bergkvist L, Adami H O, Persson I, Hoover R, Schairer C, 1989, "The risk of breast cancer after estrogen and estrogen-progestin replacement", N Eng J Med, 321:293–297; Colditz G A, Hankinson S E, Hunter D J, Willett W C, Manson J E, Stampfer M J, Hennekens C, Rosner B, Speizer F E, 1995, "The use of estrogens and progestins and the risk of breast cancer in postmenopausal women", N Eng J Med, 332(24):1589–1593).

Oocytes are formed early in life as the oogonia enter into meiosis in the fetal ovary. Early in prophase 1, the oocytes are arrested in the diplotene stage and remain arrested until the final steps of oocyte maturation, which are initiated by the resumption of meiosis at puberty and onwards. During this process of follicular development the oocyte undergoes a dramatic growth phase, during which the oocyte acquires the competence to complete the meiotic process. As a consequence of LH rise in plasma the oocyte inside the pre-ovulatory Graafian follicle will resume meiosis and undergo the final maturation that is a prerequisite for subsequent fertilization after ovulation.

The mechanism by which primordial follicles are recruited is per se largely unknown.

SUMMARY OF THE INVENTION

The present invention provides a method to protect the LH-receptors in brain and ovary against increasing amplitudes of gonadotropins especially LH, thereby protecting against hot flushes and reducing the rate of follicle loss from the ovaries, deferring the onset of menopause and consequently the symptoms related to lack of estrogen.

Furthermore the present invention provides a method for contraception by blocking the LH action on the follicle and thereby inhibiting oocyte maturation and subsequent fertilization.

Using LH-receptor antagonists will not alter the FSH and LH output from the pituitary and thereby not effect the important FSH/estrogen/GNRH (gonadotropin releasing hormone) feedback. Using potent/complete LH-receptor antagonists may be associated with altered mechanism or eventual inhibition of ovulation and luteinization of the follicle resulting in a reduced level of plasma progesterone. The invention may be used in combination with supplementary progesterone if needed.

An object of the invention is to provide a pharmaceutical composition for deferring the menopause.

Another object of the invention is to provide a pharmaceutical composition for treating hot flushes or hot flashes.

A further object of the invention is to provide a pharmaceutical composition for treating estrogen deficiencies in peri-menopausal women.

Further objects will become apparent from the following description.

DETAILED DESCRIPTION OF THE INVENTION

In one aspect the present invention relates to a pharmaceutical composition comprising an LH antagonist or a pharmaceutically acceptable salt thereof, and a pharmaceutically acceptable excipient, carrier or diluent. The LH antagonist is one that diminishes or blocks some or all of the biological effects of endogenous secreted LH. Preferably the LH antagonist diminishes the biological effects of endogenous secreted LH thereby avoiding supplemental treatment with progesterone. Preferably the LH antagonist is a partial antagonist, such as a competitive or non-competitive antagonist.

In another aspect the present invention relates to the use of a LH antagonist or a pharmaceutically acceptable salt thereof for the preparation of a medicament for the treatment of hot flushes or hot flashes. The majority of menopausal women experience hot flushes or hot flashes and treatment with an LH antagonist during the menopause would reduce or inhibit such hot flushes or hot flashes.

In a further aspect the present invention relates to use of an LH antagonist or a pharmaceutically acceptable salt thereof for the preparation of a medicament for the treatment of estrogen deficiencies in the peri- or post-menopause, preferably in the peri-menopause. Such estrogen deficiencies may be bone loss, e.g., osteoporosis, cardiovascular diseases, cognitive disorders, senile dementia-Alzheimer's type, menopausal symptoms including flushing, urogenital atrophy, depression, mania and schizophrenia, incontinence, obesity, depression, regulation of glucose metabolism, dysmenorrhea, threatened or habitual abortion, dysfunctional uterine bleeding, acne, hirsutism, prostatic carcinoma, estrogen-dependent cancers, e.g., breast cancer and postpartum lactation; each of which estrogen deficiencies represents an embodiment of the present invention.

In a still further aspect the present invention relates to use of an LH antagonist or a pharmaceutically acceptable salt thereof for the preparation of a medicament for deferring the onset of menopause. By deferring the onset of menopause estrogen deficiencies are deferred as well.

In a further aspect the present invention relates to use of an LH antagonist or a pharmaceutically acceptable salt thereof for the preparation of a contraceptive.

In a still further aspect the present invention relates to a method for treatment of hot flushes or hot flashes, comprising administering to a subject in need thereof, an effective amount of an LH antagonist or a pharmaceutically acceptable salt thereof.

In a further aspect the present invention relates to a method for treatment of estrogen deficiencies in the peri-menopause, comprising administering to a subject in need thereof, e.g., a woman, an effective amount of an LH antagonist or a pharmaceutically acceptable salt thereof.

In a still further aspect the present invention relates to a method for deferring the onset of menopause, comprising administering to a subject in need thereof, e.g., a woman, an effective amount of an LH antagonist or a pharmaceutically acceptable salt thereof.

In a further aspect the present invention relates to a method for prevention of pregnancy, comprising administering to a subject in need thereof, e.g., a woman, an effective amount of an LH antagonist or a pharmaceutically acceptable salt thereof.

In a still further aspect the present invention relates to a method of detecting an LH antagonist, comprising subjecting one or more compounds to a) an in vitro binding assay substantially as described in Acta Endocrinol. Vol. 121, 1 pp. 46–54, (1989), to determine LH-receptor binding affinity, and b) an in vitro assay substantially as described in Tertrin-Clary et al. (1980) FEBS LETTERS, Vol. 118, 1 pp. 77–80, to determine functional LH receptor interaction. The term "substantially" means that minor modifications known to the skilled person(s) may be introduced using standard principles known in the art.

Whether a molecule have both LH-receptor binding affinity and functional LH receptor interaction are determined using standard principles known in the art.

In one embodiment the LH antagonist or a pharmaceutically acceptable salt thereof may be used for treatment of hot flushes or hot flashes.

In another embodiment the LH antagonist or a pharmaceutically acceptable salt thereof may be used for the treatment of estrogen deficiencies in the peri-menopause.

In a further embodiment the LH antagonist or a pharmaceutically acceptable salt thereof may be used for deferring the onset of menopause in a woman.

In a still further embodiment the LH antagonist or a pharmaceutically acceptable salt thereof may be used as a contraceptive.

In a further embodiment the LH antagonist or a pharmaceutically acceptable salt thereof is administered to a subject in need thereof, as a dose with an effective amount in the range from about 0.01 mg to about 100 g per subject per day, preferably from about 1 to about 1000 mg per patient per day.

In a still further embodiment the LH antagonist or a pharmaceutically acceptable salt thereof is combined with supplementary administration of progesterone, which progesterone may be administered in the range from about 0.01mg to about 100 g per subject per day.

In a further embodiment the LH antagonist is a compound having a molecular weight of less than 1500 Daltons comprising within its structure a cyclic moiety of formula (I)

(I)

wherein X, attached to a carbon atom, represents O, S or NH, and ring A, containing within its structure the carbon atom whereto X is attached, represents a saturated, unsaturated or aromatic system being a 5- to 6-membered monocyclic system containing one to six carbon atom(s) and optionally one to five hetero atom(s) selected from nitrogen, sulfur and oxygen or 9- to 10-membered fused system containing four to ten carbon atom(s) and optionally one to six hetero atom(s) selected from nitrogen, sulfur and oxygen or 13- to 14-membered fused system containing seven to fourteen carbon atom(s) and optionally one to seven hetero atom(s) selected from nitrogen, sulfur and oxygen; optionally substituted with one or more $C_{1-6}$alkyl, such as methyl, ethyl, propyl, isopropyl, butyl, sec-butyl or tert-butyl; cyano, halogen, such as chloro, bromo, iodo or fluoro; or aryl, such as phenyl. In a preferred embodiment X is O. In another preferred embodiment the compound comprises within its structure one or more, preferably one cyclic moiety or two cyclic moieties independently selected from formula (I). In a further embodiment the 5- to 6-membered monocyclic system contain zero, one or two hetero atom(s) selected from nitrogen. In another embodiment the 9- to 10-membered fused system contain one, two or three hetero atom(s) independently selected from nitrogen and oxygen. In further embodiment the 13- to 14-membered fused system contain one, two or three hetero atom(s) independently selected from nitrogen and oxygen. In a still further embodiment the LH antagonist is a compound having a molecular weight of from 200 to 1000 Daltons, such as 200 to 800 Daltons, comprising within its structure a cyclic moiety of formula (I).

Preferred cyclic moieties of formula (I) are selected from

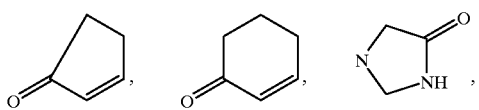

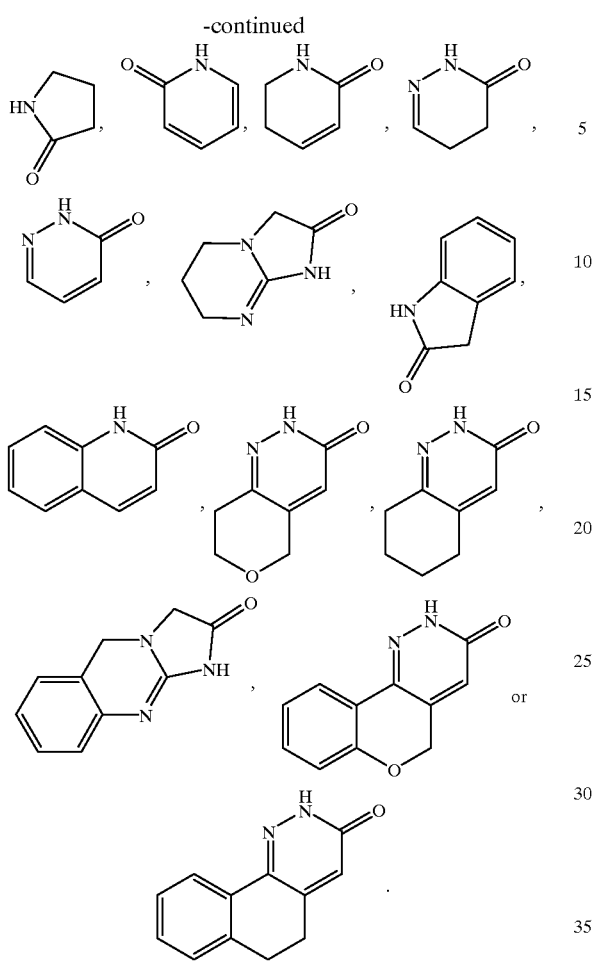

In further embodiments the LH antagonist is NG-LH, milrinone, cilostamide, amrinone, enoximone, CI-930, anagrelide, pimobendan, siguazodan (SKF-94836), lixazinone (RS-82856), imazodan (CI-914), indolidan (LY195115), quazinone, SKF 94120, Org 30029, adibendan (BM 14,478), APP 201-533, carbazeran, cilostazole, E-1020, IPS-1251, nanterinone (UK-61260), pelrinone, RMI 82249, UD-CG 212, bemarinone (ORF-16,600) CK-2130, motapizone, OPC-3911, Ro 13-6438, sulmazole, vesnarinone (OPC-8212), buquineran, DPN 205-734, ICI-170777, isomazole (LY175326), MCI-154, MS-857, OPC-8490, piroximone (MLD 19205), RS-1893, saterinone, ZSY-39, ICI 118233, and the following compounds

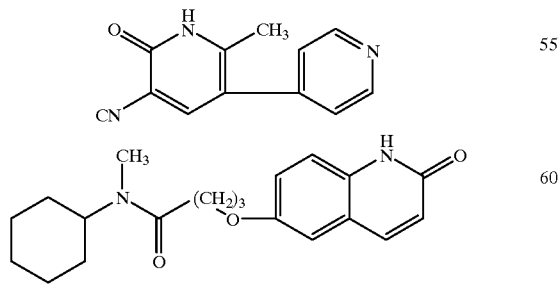

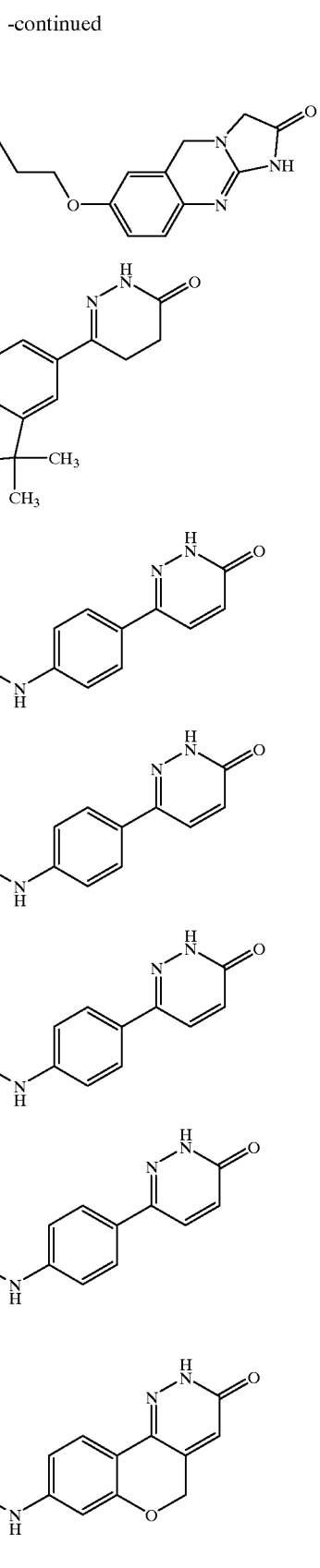

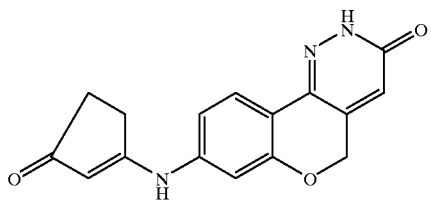

or

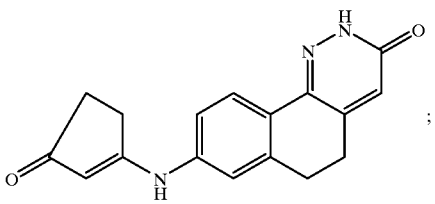

or a pharmaceutically acceptable salt thereof. Each of the above mentioned compounds represents an embodiment of the present invention.

The effective, such as the therapeutically effective, amount of an LH antagonist will depend upon the mode of administration, on the therapy desired, form in which administered, the subject to be treated and the body weight of the subject to be treated, and the preference and experience of the physician or veterinarian in charge.

As used herein the term "patient" or "subject" comprises any mammal which may benefit from treatment with an LH antagonist, such as a human, in particular a woman, either in the pre-, peri- or post-menopausal period. However, "patient" or "subject" is not intended to be limited to a woman.

As used herein the term "treatment" is also meant to comprise prophylactic treatment.

As used herein the term "LH antagonist" or "LH-receptor antagonist" is intended to comprise any compound, e.g., antibody, small molecule, peptide, oligopeptide, polypeptide or protein, preferably small molecule or peptide, that exhibits partial, complete, competitive and/or non-competitive antagonistic effect on mammalian, preferably the human, LH-receptors, thus diminishing or blocking, preferably diminishing, some or all of the biological effects of endogenous secreted LH. An example of anLH antagonist is nitroguanidyl-lutropin (NG-LH) disclosed in FEBS LETTERS, Vol. 118, no.1, p. 77–80, August 1980. There is no mentioning of a pharmaceutical effect. Other examples of suitable LH antagonists are selected from the group consisting of milrinone, cilostamide, amrinone, enoximone, CI-930, anagrelide, pimobendan, siguazodan (SKF-94836), lixazinone (RS-82856), imazodan (CI-914), indolidan (LY195115), quazinone, SKF 94120, Org 30029, adibendan (BM 14,478), APP 201-533, carbazeran, cilostazole, E-1020, IPS-1251, nanterinone (UK-61260), pelrinone, RMI 82249, UD-CG 212, bemarinone (ORF-16,600) CK-2130, motapizone, OPC-3911, Ro 13-6438, sulmazole, vesnarinone (OPC-8212), buquineran, DPN 205-734, ICI-170777, isomazole (LY175326), MCI-154, MS-857, OPC-8490, piroximone (MLD 19205), RS-1893, saterinone, ZSY-39, ICI 118233, and the following compounds

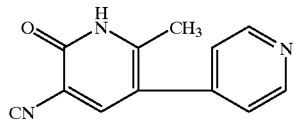

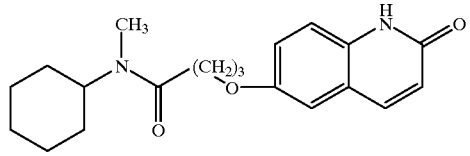

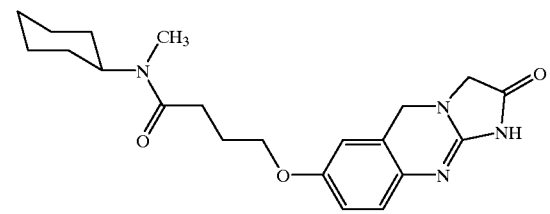

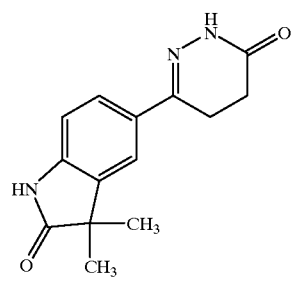

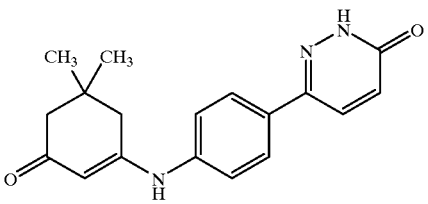

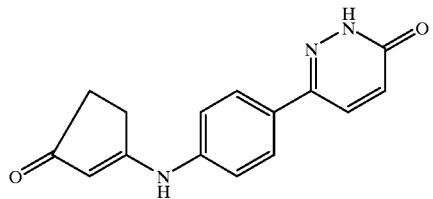

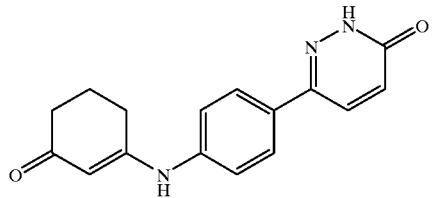

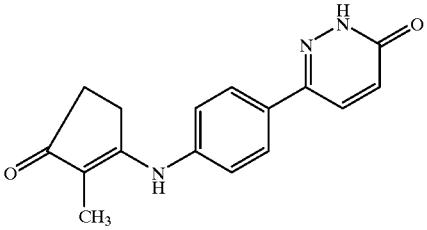

-continued

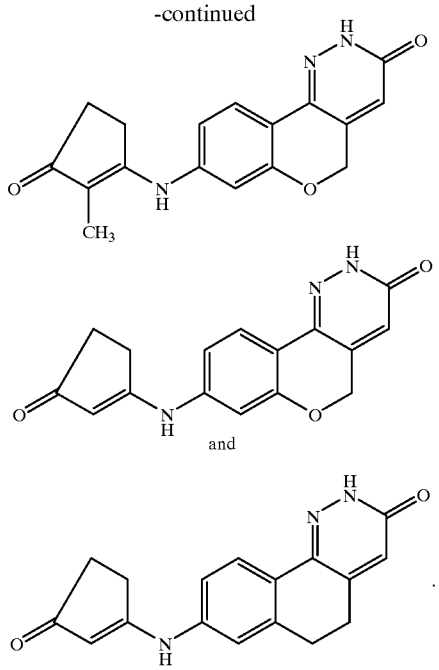

The present invention is by no means limited to any of the above mentioned compounds, which are only for illustrative purposes.

Within the present invention, the LH antagonists may be prepared in the form of pharmaceutically acceptable salts, especially acid-addition salts, including salts of organic acids and mineral acids. Examples of such salts include salts of organic acids such as formic acid, fumaric acid, acetic acid, propionic acid, glycolic acid, lactic acid, pyruvic acid, oxalic acid, succinic acid, malic acid, tartaric acid, citric acid, benzoic acid, salicylic acid and the like. Suitable inorganic acid-addition salts include salts of hydrochloric, hydrobromic, sulphuric and phosphoric acids and the like. Further examples of pharmaceutically acceptable inorganic or organic acid addition salts include the pharmaceutically acceptable salts listed in Journal of Pharmaceutical Science, 66, 2 (1977) which are known to the skilled artisan.

Also intended as pharmaceutically acceptable acid addition salts are the hydrates which the present LH antagonists are able to form.

The acid addition salts may be obtained as the direct products of compound synthesis. In the alternative, the free base may be dissolved in a suitable solvent containing the appropriate acid, and the salt isolated by evaporating the solvent or otherwise separating the salt and solvent.

The LH antagonists may form solvates with standard low molecular weight solvents using methods known to the man skilled in the art.

The LH antagonists may be administered in pharmaceutically acceptable acid addition salt form or, where appropriate, as a alkali metal or alkaline earth metal or lower alkylammonium salt. Such salt forms are believed to exhibit approximately the same order of activity as the free base forms.

Pharmaceutical Compositions

A pharmaceutical composition for use in accordance with the present invention comprises, an LH antagonist, or a pharmaceutically acceptable salt thereof, together with a pharmaceutically acceptable carrier. The composition may comprise one or more LH antagonist(s) as active ingredient (s), together with one or more pharmaceutically acceptable carrier(s).

Pharmaceutical compositions containing LH antagonists may be prepared by conventional techniques, e.g. as described in Remington: The Science and Practise of Pharmacy, 19$^{th}$ Ed., 1995. The compositions may appear in conventional forms, for example, capsules, tablets, aerosols, solutions, suspensions or topical applications.

The dosage of an LH antagonist required to block the LH action on the follicle or decrease the loss of folicles during the pre- and peri-menopausal period will depend on the specific compound and the route of administration, as described below. Generally, an effective dosage to decrease the loss of folicles will be a dose of about 0.0001 to about 10 mg/kg of compound once or twice per day. For specific compounds listed herein, further guidance to effective dosages can be obtained from the manufacturers' recommended dosages.

The dose is determined in part based on the pharmacokinetics of the LH antagonist employed using standard pharmacokinetics principles known in the art.

Typical compositions include an LH antagonist or a pharmaceutically acceptable acid addition salt thereof, associated with a pharmaceutically acceptable excipient which may be a carrier or a diluent or be diluted by a carrier, or enclosed within a carrier which can be in the form of a capsule, sachet, paper or other container. In making the compositions, conventional techniques for the preparation of pharmaceutical compositions may be used. For example, the active compound will usually be mixed with a carrier, or diluted by a carrier, or enclosed within a carrier which may be in the form of a ampoule, capsule, sachet, paper, or other container. When the carrier serves as a diluent, it may be solid, semi-solid, or liquid material which acts as a vehicle, excipient, or medium for the active compound. The active compound can be adsorbed on a granular solid container for example in a sachet. Some examples of suitable carriers are water, salt solutions, alcohol's, polyethylene glycol's, polyhydroxyethoxylated castor oil, peanut oil, olive oil, gelatine, lactose, terra alba, sucrose, cyclodextrin, amylose, magnesium stearate, talc, gelatine, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone. Similarly, the carrier or diluent may include any sustained release material known in the art, such as glyceryl monostearate or glyceryl distearate, alone or mixed with a wax. The formulations may also include wetting agents, emulsifying and suspending agents, preserving agents, sweetening agents or flavouring agents. The formulations of the invention may be formulated so as to provide quick, sustained, or delayed release of the active ingredient after administration to the patient by employing procedures well known in the art. In the present specification "carrier" is intended to comprise all of the above possibilities, such as diluents, carriers, fillers, excipients and the like.

The pharmaceutical compositions can be sterilized and mixed, if desired, with auxiliary agents, emulsifiers, salt for influencing osmotic pressure, buffers and/or coloring substances and the like, which do not deleteriously react with the active compounds.

The route of administration may be any route, which effectively transports the active LH antagonist to the appropriate or desired site of action, such as oral, nasal, pulmonary, transdermal, such as passive or iontophoretic delivery, or parenteral, e.g., rectal, depot, subcutaneous, intravenous, intraurethral, intramuscular, intranasal, ophthalmic solution or an ointment.

If a solid carrier is used for oral administration, the preparation may be tabletted, placed in a hard gelatine capsule in powder or pellet form or it can be in the form of a troche or lozenge. If a liquid carrier is used, the preparation may be in the form of a syrup, emulsion, soft gelatin capsule or sterile injectable liquid such as an aqueous or non-aqueous liquid suspension or solution.

For nasal administration, the preparation may contain an LH antagonist dissolved or suspended in a liquid carrier, in particular an aqueous carrier, for aerosol application. The carrier may contain additives such as solubilizing agents, e.g., propylene glycol, surfactants, absorption enhancers such as lecithin (phosphatidylcholine) or cyclodextrin, or preservatives such as parabenes.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

A typical tablet which may be prepared by conventional tabletting techniques may contain:
Core:

| Core: | |
|---|---|
| Active LH antagonist (as free compound or salt thereof) | 10 mg |
| Colloidal silicon dioxide (Aerosil) | 1.5 mg |
| Cellulose, microcryst. (Avicel) | 70 mg |
| Modified cellulose gum (Ac-Di-Sol) | 7.5 mg |
| Magnesium stearate | Ad. |
| Coating: | |
| HPMC approx. | 9 mg |
| *Mywacett 9-40 T approx. | 0.9 mg |

*Acylated monoglyceride used as plasticizer for film coating.

Any novel feature or combination of features described herein is considered essential to this invention.

EXAMPLES

1) Human luteinizing hormone (hLH)

hLH is a glyco-protein hormone that is synthesized and secreted from the anterior pituitary gland. LH is a dimer that consists of two protein chains (an alpha-chain and a beta-chain) held together by non-covalent, ionic interactions. The alpha-chain in LH is identical to the alpha-chain in two other pituitary dimer gluco-protein hormones namely FSH and thyroid stimulating hormone (TSH) thus the beta-chain is being responsible for the hormone specific action of these hormones.

The LH hormone is secreted to the circulating blood and by this route reach the target cells which express the membrane bound LH receptor. The biological plasma half-life of LH is very short (minutes). (REF: The Physiology of Reproduction. Eds. Knobil, E. & Neill, J. D. pp. 487–540, Raven Press, New York, 1994).

2) Screening Assays

The human LH-receptor has been identified, sequenced and cloned. This receptor will be expressed in different transformed cell lines fused to reporter systems (Gi-protein coupled messages). Both receptor binding and a functional activation assay will be used to screen compounds. Compounds that binds to the receptor but do not activate the receptor will be tested in ex-vivo and in vivo models for their ability to counteract LH action.

The ex vivo system will consists of isolated cultured mouse follicles that responds to LH added to the culture medium by inducing oocyte maturation.

A screening tree comprising some or all of the following battery of assay are employed to test compound libraries and de novo synthesised compounds for LH antagonistic properties:

A) An in vitro assay to determine functional LH receptor interaction is used (like the cAMP assay using rat ovarian homogenates as described in Tertrin-Clary et al. (1980) FEBS LETTERS, Vol. 118, 1 pp. 77–80). LH will serve as a positive control elevating the cAMP level from base line and a compound exhibiting antagonistic effect will decrease the cAMP accumulation from base line.

B) An in vitro binding assay using displacement/interaction of compounds with [125I]-hCG binding to mouse ovarian homogenate (modified from Ding and Huhtaniemi (1989) Acta Endocrinol. Vol. 121, 1 pp. 46–54) is used to screen for LH-receptor affinity. Compounds that display affinity to the LH-receptor will significantly displace the [125I] labelled hCG.

C) A commercially available cell line expressing the cloned human LH receptor using a cAMP reporter gene (Christinmaitre & Bouchard (1996) Molecular and Cellular Endocrinology Vol. 125, 1–2 pp. 151–159) is used to test the compounds antagonistic effect towards supplemented LH.

D) An ex vivo culture system of rodent follicles (Lindner et al. (1974) Res. Prog. Horm. Res. Vol. 30, pp.79–138) is used to evaluate the compounds ability to counteract the action of LH on steroidogenesis and oocyte maturation. Compounds that inhibits oocyte maturation are drug candidates for contraception.

E) An in vivo hot flush model is used to test the compounds direct effects on the skin temperature response to naloxone in morphine-dependent rats (Katovich & O'Meara (1987) Can. J. Physiol. Pharmacol. Vol. 65 pp. 563–567). The compounds indirect effect on hot flushes due to deferring the onset of menopause can not be tested in this particular assay.

F) Transgenic mice over-expressing the LHβ subunit is used to test the compounds in vivo effect to protect the ovaries from rapid follicle loss. Compounds that reverse the phenotype of LHβ subunit transgenic mice, namely the accelerated follicle loss, are drug candidates for deferring the onset of menopause in women reversing the accelerated loss of follicle experienced in the pre-menopausal period.

What is claimed is:

1. A method for treatment of hot flushes or hot flashes comprising administering to a subject in need thereof an effective amount of a luteinizing hormone antagonist or a pharmaceutically acceptable salt thereof.

2. The method according to claim 1, wherein the luteinizing hormone antagonist or pharmaceutically acceptable salt thereof is administered as a dose with an effective amount in the range from about 0.01 mg to about 100 g per day.

3. The method according to claim 1, wherein the subject is a woman.

4. A method for treatment of estrogen deficiencies comprising administering to a subject in need thereof an effective amount of a luteinizing hormone antagonist or a pharmaceutically acceptable salt thereof.

5. A method for deferring the onset of menopause comprising administering to a subject in need thereof an effective amount of a luteinizing hormone antagonist or a pharmaceutically acceptable salt thereof.

6. A method according to claim 1, wherein the luteinizing hormone antagonist is a compound having a molecule weight of less than 1500 Daltons comprising within its structure a cyclic moiety of formula (I)

(I)

wherein X, attached to a carbon atom, represents O, or S or NH, and ring A, containing within its structure the carbon atom whereto X is attached, represents a saturated, unsaturated or aromatic system being a 5- to 6-membered monocyclic system containing one to six carbon atom(s) and optionally one to five hetero atom(s) selected from nitrogen, sulfur and oxygen or 9- to 10-membered fused system containing four to ten carbon atom(s) and optionally one to six hetero atom(s) selected from nitrogen, sulfur and oxygen or 13- to 14-membered fused system contaning seven to fourteen carbon atom(s) and optionally one to seven hetero atom(s) selected from nitrogen, sulfur and oxygen; opotionally substituted with one or more $C_{1-6}$alkyl, cyano, halogen or aryl.

7. The method of claim 6, wherein the $C_{1-6}$alkyl is methyl, ethyl, propyl, isopropyl, butyl, sec-butyl or tert-butyl.

8. The method of claim 6, wherein the halogen is chloro, bromo, iodo or fluoro.

9. The method of claim 6, wherein the aryl is phenyl.

10. The method according to claim 1, wherein the luteinizing hormone antagonist is nitroguanidyl-lutropin, milrinone, cilostamide, amrinone, enoximone, anagrelide, pimobendan, siguazodan, lixazinone, imazodan, indolidan, quazinone, adibendan, carbazeran, cilostazole, nanterinone, pelrinone, bemarinone motapizone, sulmazole, vesnarinone, buquineran, isomazole piroximone, saterinone,

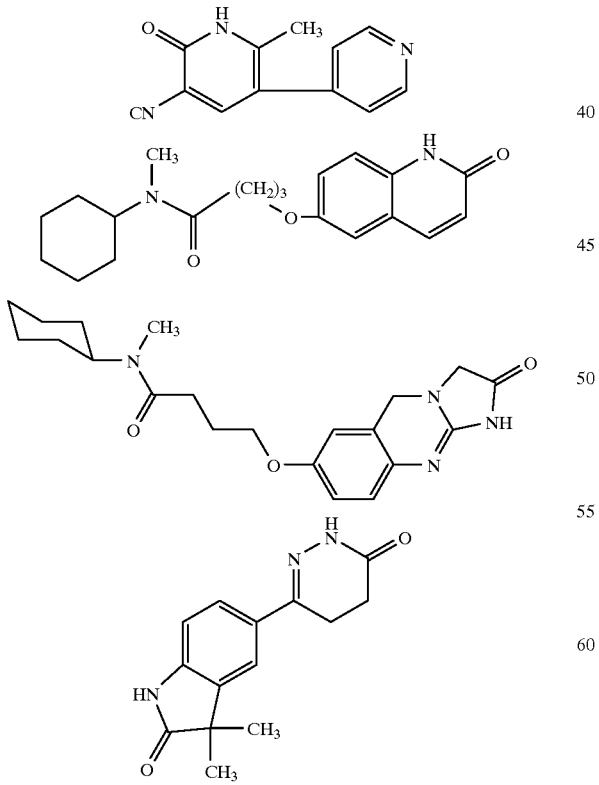

-continued

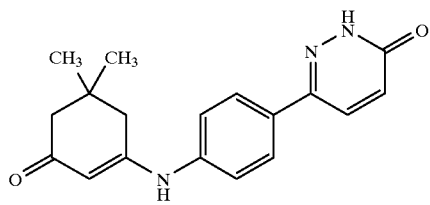

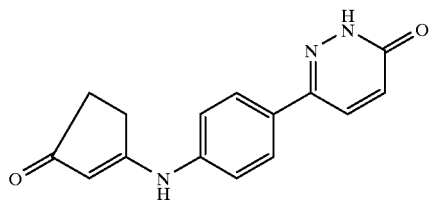

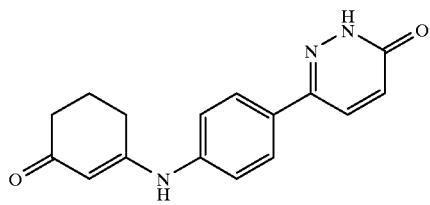

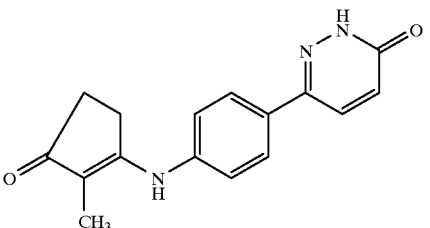

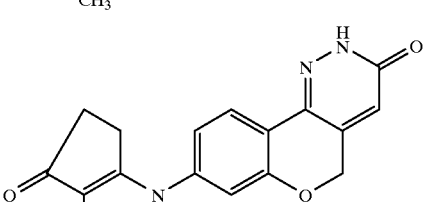

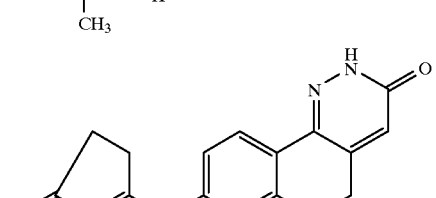

or

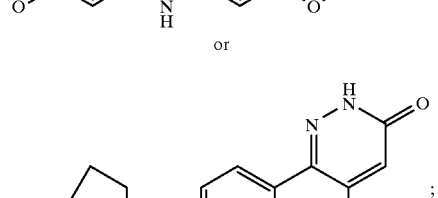

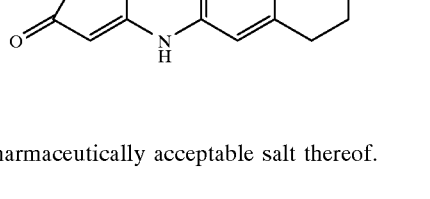

;

or a pharmaceutically acceptable salt thereof.

* * * * *